United States Patent [19]

Green et al.

[11] Patent Number: 4,641,329

[45] Date of Patent: Feb. 3, 1987

[54] FIXTURE FOR SUPPORTING AND ALIGNING A SAMPLE TO BE ANALYZED IN AN X-RAY DIFFRACTION APPARATUS

[75] Inventors: Lanny A. Green; Joaquim L. Heck, Jr., both of Knoxville, Tenn.

[73] Assignee: The United States of America as represented by the United States Department of Energy, Washington, D.C.

[21] Appl. No.: 726,562

[22] Filed: Apr. 23, 1985

[51] Int. Cl.$^4$ .............................................. G01N 23/20
[52] U.S. Cl. ........................................ 378/79; 378/70; 378/71; 378/73; 378/74; 378/81
[58] Field of Search ..................................... 378/70–81; 51/216 A

[56] References Cited

U.S. PATENT DOCUMENTS 2,431,282  11/1947  Speed ................................. 51/216 A
2,445,132   7/1948  Berman .................................. 378/78
3,536,912  10/1970  Speck et al. ........................... 378/79
3,600,576   8/1971  Carter et al. ........................... 378/80

Primary Examiner—Craig E. Church
Assistant Examiner—John C. Freeman
Attorney, Agent, or Firm—Earl L. Larcher; Stephen D. Hamel; Judson R. Hightower

[57]     ABSTRACT

A fixture is provided for supporting and aligning small samples of material on a goniometer for X-ray diffraction analysis. A sample-containing capillary is accurately positioned for rotation in the X-ray beam by selectively adjusting the fixture to position the capillary relative to the x and y axes thereof to prevent wobble and position the sample along the z axis or the axis of rotation. By employing the subject fixture relatively small samples of materials can be analyzed in an X-ray diffraction apparatus previously limited to the analysis of much larger samples.

7 Claims, 5 Drawing Figures

FIXTURE FOR SUPPORTING AND ALIGNING A SAMPLE TO BE ANALYZED IN AN X-RAY DIFFRACTION APPARATUS

This invention is made as a result of work under contract DE-AC05-804R21400 between Martin Marietta Energy Systems, Inc. and the U.S. Department of Energy.

BACKGROUND OF THE INVENTION

The invention is directed to a fixture in which a relatively small sample of material may be analyzed by X-ray diffraction, and more particularly to such fixtures wherein the sample is supported in alignment for analysis on an X-ray diffraction goniometer previously limited to the analysis of relatively large samples.

X-ray diffraction has become a commonly employed tool for non-destructively analyzing material for determining the chemical composition, the microstructural characteristics, and other properties of the material. If a sufficient quantity of the material to be analyzed is available, a computer coupled goniometer system may be suitably employed for the X-ray diffraction process. In such a goniometer system an X-ray beam from an X-ray generator is projected across a sample and X-ray beam diffractions emanating therefrom are picked up by a detector rotated through various incremental angles. The sample is rotated one degree for every two degrees of rotation of the detector in order to satisfy the Bragg equation for the proper analysis of the sample by X-ray diffraction. Goniometers suitable for X-ray diffraction and adaptable for use with the present invention include such systems as the commercially available system known as D-500 Diffractometer provided by Siemens-Allis, Inc., Cherry Hill, N.J.

In the analysis of a material by X-ray diffraction with known goniometers and if a sufficient quantity of the material is available, a selected portion of this material can be conventionally mounted on a glass fixture or stationed on a holder which in turn is positioned on a rotatable mount for rotation about a central axis during the exposure of the material to an X-ray beam in contact therewith. The collimated X-ray beam emanating from a fixed X-ray beam generator is directed through the material and the diffracted X-rays are detected with an electronic X-ray beam detector which is positioned radially outwardly from the sample holder and is also rotated through an arc starting at an initial two theta angle of approximately 12° to 15°, to a final two theta angle of approximately 160° during the X-ray analysis. The resulting diffractogram is electronically processed in a suitable computer which provides comparisons of the derived data with diffractograms of known materials to analyze the material. This electronic analysis is very rapid and is considered to be highly accurate.

However, X-ray diffraction by using computer-coupled goniometers has not been possible in instances where only relatively small quantities of the material to be analyzed are available since the known apparatus and sample-holding fixtures utilized in such goniometers for relatively large samples cannot be used. Previously, when only relatively small samples of material were available for analysis the sample was subjected to X-ray analysis by mounting the sample in a small glass capillary and then positioning the loaded capillary in the center of a small concave receptacle. A strip of undeveloped film is placed around the sample against the walls of the receptacle and then an X-ray beam is projected through a hole in the wall of the receptacle onto the capillary to record a diffractogram of the sample on the film. The film then must be developed, analyzed and then compared to the diffractograms of known substances in order to determine the characteristics or properties of the sample. This procedure has been found to be cumbersome, time consuming, and often sufficiently inaccurate to render questionable the overall process.

SUMMARY OF THE INVENTION

Accordingly, it is the primary aim or objective of the present invention to provide a fixture or mounting device by which small samples of material contained in or on a capillary that is supported and aligned on a goniometer previously useable for only relatively large samples for X-ray diffraction analysis. Generally, this fixture supports and aligns the sample in an X-ray beam projecting from an X-ray source to an X-ray detector mounted for rotation about a first axis for effecting X-ray analysis of the sample. The fixture comprises a base supported for rotation about the first axis and disposed at a location intermediate the X-ray beam source and the X-ray detector. First and second plate means are carried by the base means in a stacked array along the first axis and are provided with juxtaposed planar surfaces disposed normal to the first axis. Yieldable means secure the first plate (the outermost plate) to the second plate means (the innermost plate) for urging the plate means toward one another. Boss means are centrally disposed on a surface of the first plate means and extend along the first axis. A sample supporting means is moveably attached to the boss means for selective longitudinal movement along the first axis and is provided with an elongated receptacle therein which extends along the first axis for receiving and supporting a sample-containing capillary on the first axis. Selectively adjustable spacer means tilt or displace the first plate means along at least one other axis for positioning and maintaining the sample containing capillary on the first axis during rotation of the base means.

This fixture construction provides for the X-ray diffraction of small samples in a conventional X-ray diffraction goniometer since by using the tiltable plate means the sample-containing capillary may be adjusted relative to the xy plane by tilting the plate to assure rotation of the capillary on the z axis without wobble or other rotational disturbances which would detract from the X-ray diffraction analysis. Also, by moving the sample supporting means along the first axis the capillary can be properly longitudinally positioned along the z axis for X-ray analysis.

The yieldable means used to attach together the first and second plate means comprises spring means which are disposed between the first and second plate means at a location adjacent to a peripheral edge thereof for urging the outer or first plate means towards the inner or second discoidal plate means. A pivot point is established between the first and second plate means at a location adjacent to the spring means for providing a pivot about which the sample supporting means of the first plate means may be tilted or displaced along the said at least one other axis. This tilting of the first plate means is achieved by selectively moving the adjustable spacer means which comprise a pair of elongated threaded rod means that are threadedly coupled with and extend through the first plate means in a direction parallel to the first axis at locations on opposite sides of the boss means and bear against the planar surface of the inner or second plate means. The rotation of one of the pair of elongated threaded rod means displaces or tilts the sample supporting means along a second axis perpendicular to the first axis and the rotation of the other of said pair of elongated rod means tilts the sample supporting means along a third axis which is perpendicular to both the first axis and the second axis. This tilting of the outermost plate by the selective movement of the threaded rods correctly aligns the sample-containing capillary on the z axis for X-ray diffraction.

Other and further objects of the invention will be obvious upon an understanding of the illustrative embodiment about to be described or will be indicated in the appended claims, and various advantages not referred to herein will occur to one skilled in the art upon employment of the invention in practice.

A preferred embodiment of the invention has been chosen for the purpose of illustration and description. The preferred embodiment illustrated is not intended to be exhaustive or to limit the invention to the precise form disclosed. It is chosen and described in order to best explain the principles of the invention and their application in practical use to thereby enable others skilled in the art to best utilize the invention in various embodiments and modifications as are best adapted to the particular use contemplated.

DETAILED DESCRIPTION OF THE INVENTION

As briefly described above the present invention is directed to a fixture for aligning and supporting a sample-containing capillary in a proper position for X-ray analysis by an X-ray diffraction system known as a goniometer. The X-ray diffraction goniometer shown at 10 in FIG. 1 conventionally comprises a base assembly 12 which supports an X-ray beam generator which is fixed in a stationary position on the base assembly 12. An X-ray beam 16 is projected from the X-ray generator 14 through conventional cross sectional area controlling slits or apertures 18 used for regulating the size of the X-ray beam which usually depends upon the quantity of the sample being analyzed and the portion of the sample being contacted by the X-ray beam.

Figure 1:
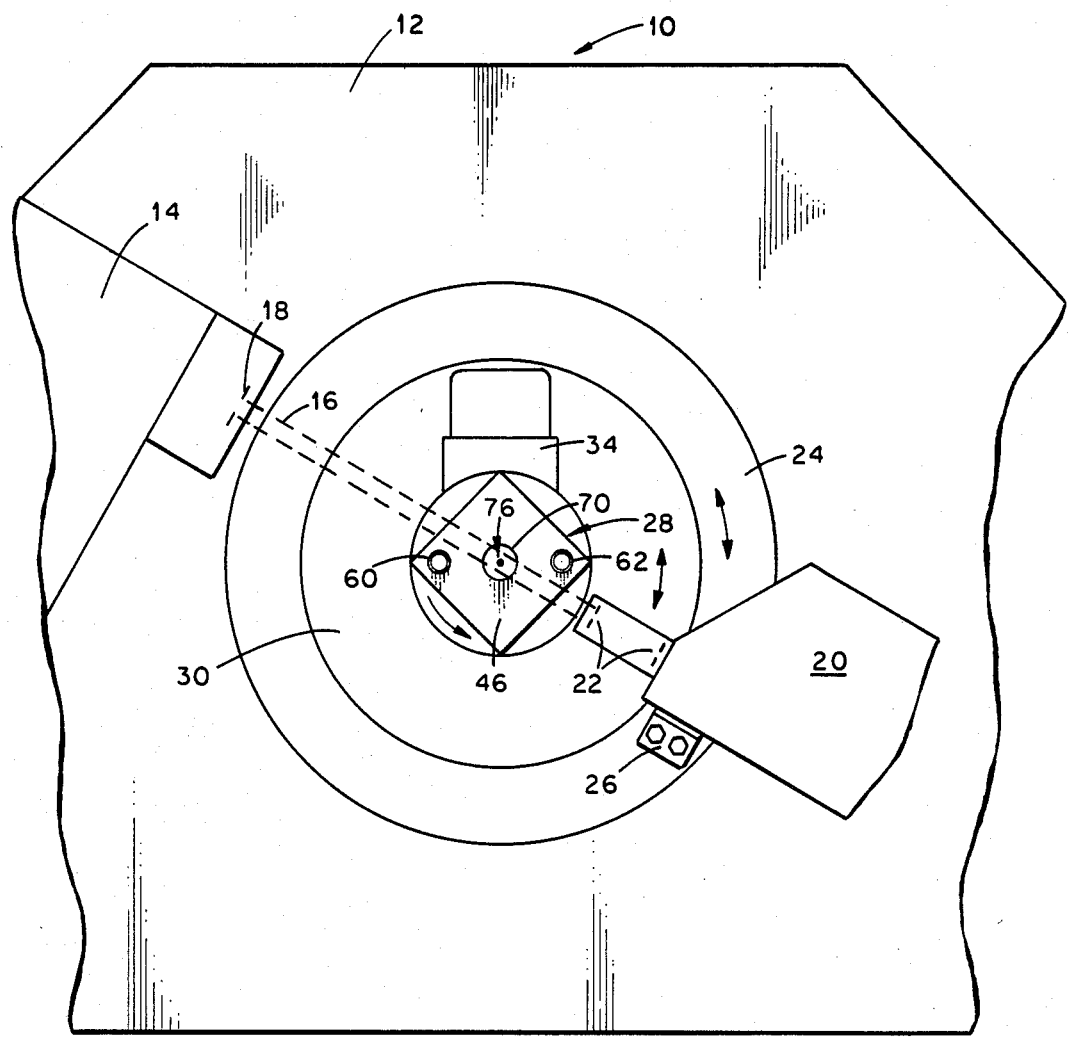
FIG. 1 is a front elevational view generally showing a goniometer system utilized for X-ray diffraction analysis of a sample supported and aligned in the X-ray beam at the alignment position by the fixture of the present invention.

An X-ray beam detector 20 intercepts the X-ray beam 16 diffracted from the sample with the diffracted X-ray beam passing through adjustable apertures 22 carried by the detector 20. The diffracted X-ray beam 16 intercepted by the X-ray detector 20 is passed through a suitable monochromometer such as a graphite monochromometer to a computer system (not shown) used to analyze the data received from the diffraction in order to analyze the chemical and physical properties of the sample and to make comparisons electronically with known materials. The X-ray detector 20 is mounted on a ring or annulus 24 for rotation about a central or z axis 25 (FIG. 3) on the base assembly 12. This rotational axis of the detector 20 is referred to as the two theta angle which provides rotation about the longitudinal axis upon which the sample is mounted. A two theta angle of 0° occurs when the detector is diametrically opposite the X-ray source. The extent or arc provided by the rotation initiates at two theta angle of approximately 2° from diametrically opposite the X-ray beam generator 14° to 160°, in timed increments of about 0.02 to 0.05 degrees per increment. At an initial two theta angle much lower than 2°, as shown in FIG. 1, the detector absorbs an excessive amount of energy from the primary X-ray beam. The X-ray detector 20 is attached to the ring 24 by any suitable mount such as the bolting arrangement generally shown at 26.

The sample supporting and aligning fixture of the present generally shown at 28 is mounted on the rotatable disc or plate 30 carried by the base assembly 12. This rotation of the sample supporting fixture 28 is about the z axis 25. The sample disc 30 is disposed within ring 24 and rotates 1° for every 2° of rotation of the X-ray detector 20 in order to satisfy the Bragg equation used in X-ray diffraction analysis.

The sample supporting and aligning fixture 28 comprises a base 32 attached to plate 30 through a geared motor and drive assembly 34 used for rotating the sample supporting fixture 28 at a rate of approximately 12 rpm during the X-ray diffraction analysis. The sample is rotated to minimize the effects of preferred orientation.

The base 32 is shown provided with a centrally located thread boss 36 which is used for attaching a concave adapter assembly 38 which is threadedly attached to the boss 36. A set screw 40 may be utilized to assure a rigid engagement between the concave adapter 38 and the base 32.

The concave adapter, as shown, also provides a plate 42 having a planar outer surface 44. The plate 42 and the adapter 38 may be formed as separate units joined to one another by a convenient coupling mechanism such as bolts or the like or they be provided as a separate assembly. An outermost plate 46 having a planar surface 48 is positioned in a stacked arrangment upon the plate 42 so that the planar surfaces 44 and 48 are juxtaposed or positioned face-to-face and perpendicular to the z axis 25.

Figure 2:
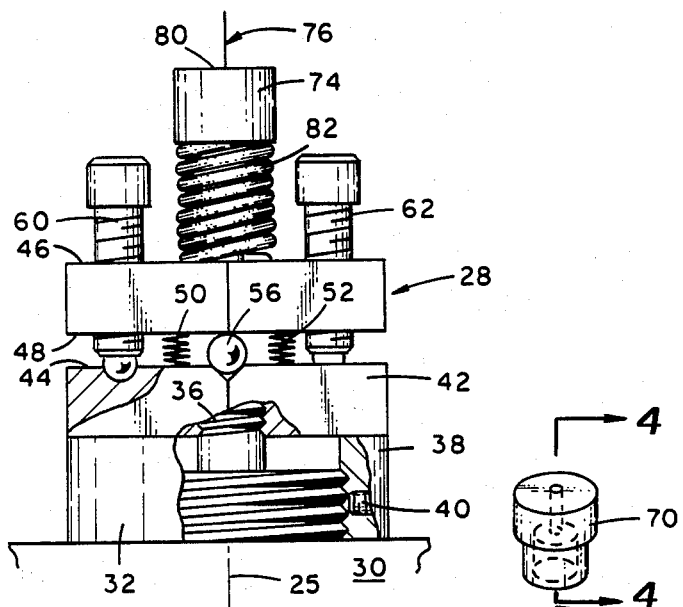
FIG. 2 is an elevational view partly broken away, of the sample holding and aligning fixture of the subject invention.
Figure 3:
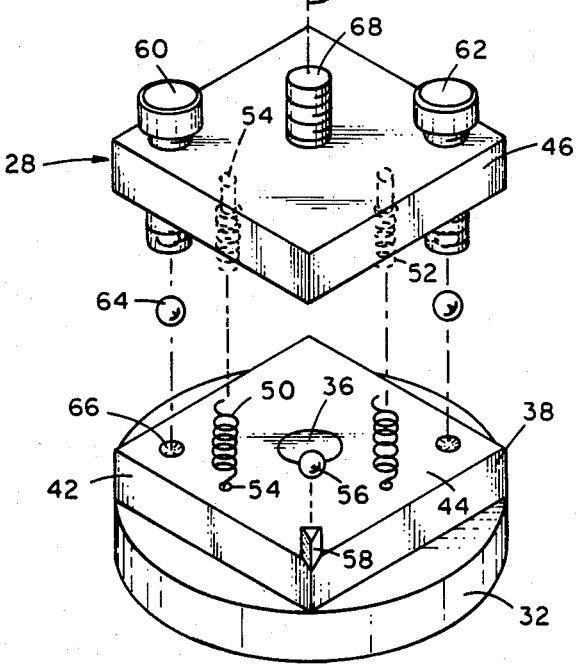
FIG. 3 is an exploded view of the FIG. 2 arrangement showing details of the fixture.

The plates 42 and 46 are secured to one another by a spring arrangement which comprises springs 50 and 52 (FIGS. 2 and 3). These springs are positioned between the plates at the surfaces thereof and are clamped to the respective plates 42 and 46 by rivets 54 or the like. The springs 50 and 52 are tension springs which urge the surfaces 44 and 48 towards one another. The two springs shown are positioned near the peripheral edge or one corner of the plates 42 and 46 to provide a tilting or a pivoting action through a pivot point provided by a ball 56 disposed intermediate the springs in a recess 58 in the planar surface 44 of plate 42. A similar recess (not shown) is in the planar surface 48 of plate 46.

As shown, the plates 42 and 46 are of a rectangular configuration but these plates may be of any desired configuration such as round or the like. Also, as shown the springs 50 and 52 are disposed adjacent to one of the corners of the rectangular plates at the spaced apart locations with the ball 56 nearer the corner and intermediate the springs 50 and 52. With this relationship of the ball 56 to the springs 50 and 52 a tilting action is provided about the ball 56 through threaded rods 60 and 62 which are disposed on opposite sides of the z axis or the rotational axis of the X-ray detector 20 and sample. The threaded rods 60 and 62 threadedly engage the upper plate 46 and bear against the planar surface 44 of the innermost plate 42 through a ball and socket arrangement 64 and 66 for facilitating the rotation of the threaded rods 60 and 62. As shown, with the rotation of the rod 60 the upper plate 46 is caused to tilt about an axis, e.g., the x axis, to align the sample along the x axis. Alternatively, the rotation of the rod 62 causes the upper plate 46 to tilt abouty the y axis. The extent of tilting required of the upper plate 46 about the x and y axis is determined during the rotation of the fixture 28 so that the plates may be correctly aligned about the x and y axis for accurately holding the sample in alignment on the z axis during rotation of the fixture as will be described in greater detail below.

Figure 4:
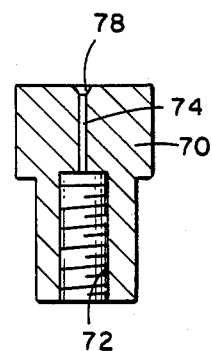
FIG. 4 is a view taken along lines 4—4 of FIG. 3 showing details of a capillary support used for supporting the samples to be analyzed by X-ray diffraction.

As best shown best in FIG. 3 the outermost plate 46 is provided with a threaded boss 68 which is centrally disposed on the plate 46 and projects along the z axis or the longitudinal axis of rotation of both the fixture 28 and the X-ray detector 20 in a direction away from the innermost planar surface 44 when the sample is properly aligned. A sample support body 70 having a knurled outer surface is threadedly coupled by a threaded bore 72 (FIG. 4) to the threaded boss 68 for displacement of the sample support 70 along the z axis when the sample support 70 is independently rotated. The sample support 70 is provided with a centrally oriented elongated receptacle 74 of a cylindrical configuration which extends along the z axis of the fixture for receiving and supporting a sample-containing capillary as generally shown at 76 in FIGS. 1 and 2. The elongated receptacle 74 is preferably provided with a chamfered or tapered upper surface 78 to facilitate the insertion of the capillary 76 into the receptacle 74. Also, a material such as clay or the like may be disposed in the receptacle 74 for holding the capillary 76 in position when it is inserted into the receptacle 74.

As shown in FIG. 2 an end portion 80 of the capillary holding the sample projects from the surface of the sample support 70 along the z axis to intercept the X-ray beam 16. A spring 82 is disposed about the boss 68 and bears against the lower surface of the support 70 to maintain a constant load or bias upon the support 70 during the rotational positioning thereof to maintain the end 80 of the capillary in the position along the z axis achieved by the rotation of the support 70.

In order to properly orient the sample containing capillary 76 in the X-ray beam 16 emanating from the X-ray beam generator 14 for reception of diffracted X-rays by the rotating detector 20 the fixture 28 is used in conjunction with an alignment system for aligning the capillary 76 in the xy plane during rotation of the fixture 28 so as to maintain the capillary 76 wobble-free on the z axis. Further, the fixture 28 and the alignment system is provided with a mechanism by which the capillary 76 may be projected longitudinally along the z axis to properly position the sample in the X-ray beam 16.

It is contemplated that several alignment systems may be used for determining the proper alignment of the sample 76 in the xy plane and z axis. For example, suitable light sensitive diodes may be disposed near the face of the detector 20 so that any wobble of the capillary due to incorrect alignment of the capillary on the x and y axes could be indicated by the differences in light received by the diodes. Also, such a light sensitive diode may be temporarily positioned on the face of the detector for indicating the correct position of the capillary 76 along the z axis.

Figure 5:
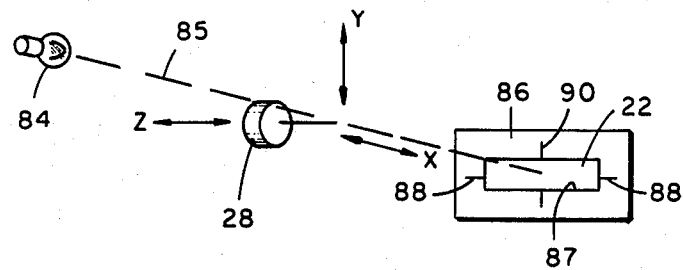
FIG. 5 is a schematic view showing an arrangement wherein the alignment of the sample-containing capillary can be correctly positioned on the x and y axes as well as the z axis for X-ray analysis in the FIG. 1 apparatus.

While several alignment systems may be utilized excellent results have been achieved by using a relatively simple alignment system generally shown in FIG. 5. In this arrangement an incandescent light source 84 is placed within in the X-ray beam generator 14 so as to project a light beam 85 through the aperture 18 across the capillary 76 to the face of the X-ray detector 20 which is placed diametrically opposite the X-ray beam generator 14 so as to receive the light beam 85 from the incandescent light 84. The light beam 85 casts a shadow indicative of the position of the capillary 76 upon the face of the detector 20. A templet 86 having a central aperture of an elongated or rectangular configuration 87 is affixed to the face of the X-ray detector 20 to provide a surface against which the shadow of the capillary 76 in the light beam may be projected. The templet 86 is preferably made from a suitable material such as white paper coated with a suitable fluorescent material so that the shadow of the capillary 76 cast thereupon may be readily discernable. The templet 86 is provided with lines 88 at the opposite ends of the rectangular aperture 87 for indicating the position of the capillary 76 and the xy plane as the capillary 76 is rotated in the fixture 28. Similarly a line 90 on the templet 86 is provided for indicating the position of the end 80 of the capillary 76 along the z axis which is achieved by the independent rotation of the sample support 70.

In a typical aligning operation a sample-containing capillary 76 is positioned in the receptacle of the sample support 70. With the fixture 28 secured in position on the goniometer 10 the incandescent light 84 is placed in the X-ray beam generator 14 to cast a beam of light 85 across the capillary 76 onto the templet 86 disposed on the face of the detector 20 which is positioned directly across from the X-ray beam generator 14 and two theta equals 0°. The fixture 28 is then rotated to cast a shadow of the capillary 76 onto the templet 86 with the shadow cast on the template 86 by the capillary being indicative of the position of the capillary 76 on the z axis and with the extent of wobble of the capillary as it is rotated being indicative of the orientation of the capillary relative to the x and/or y axis. If excessive wobble is present the rotation of the fixture is stopped and the threaded rods 60 and 62 are selectively rotated into or out of the outer plate 46 to tilt this plate 46 in the desired direction to better orient the capillary along the z axis so that during rotation of the fixture 28 only minimal or insignificant wobble is present. The rotation of the fixture and the adjustment of the threaded rods may require several sequences before proper alignment of the capillary is achieved. Upon the achieving of this essentially wobble-free operation as determined by the capillary being essentially in alignment with lines 88 on the template 86 the sample support 70 is independently rotated in a correct direction to position the end 80 of the capillary in proper alignment with lines 90 for positioning the sample in proper alignment along the z axis with the X-ray beam 16. Upon completion of the alignment, the incandescent light 84 is removed and the system is ready for X-ray analysis. A final check on system alignment may be made by observing the position of the capillary shadow in the X-ray beam on the fluorescent templet 86.

The present invention eliminates a major shortcoming in the X-ray diffraction of small samples as heretofore encountered in that it eliminates the use of the film technique considerably cuts down on the man-hours required for the X-ray diffraction of a small sample and also significantly improves the accuracy of the analysis. Another important advantage achieved by the fixture of the present invention is that X-ray analysis of the sample may be achieved by starting the initial two theta angle of the X-ray detector from a point nearly diametrically opposite the X-ray beam generator. With conventional sample holders, the initial two theta angle was physically contained to a minimum of 12 to 15 two theta degrees. The present invention eliminates a major shortcoming in the X-ray diffraction of small samples as heretofore encountered in that it eliminates the use of the film technique so as to considerably cut down on the man-hours required for the X-ray diffraction of a small sample and also significantly improve the accuracy of the analysis.

We claim:

1. A fixture for aligning and supporting a sample in a X-ray beam projecting from an X-ray source to an X-ray detector mounted for rotation about a first axis for X-ray diffraction analysis of the sample, comprising base means rotatable on said first axis and supported at a location intermediate said X-ray beam source and said X-ray detector, first and second plate means carried by and rotatable with said base means and disposed on said base means in a stacked array along said first axis and with juxtaposed planar surfaces disposed perpendicular to said first axis, yieldable means securing the first plate means to the second plate means for urging the first plate means towards the second plate means, boss means centrally disposed on a surface of said first plate means and extending along said first axis, sample supporting means movably attached to said boss means for selective movement along said first axis and having an elongated receptacle therein extending along said first axis for receiving and supporting a sample-containing capillary on said first axis, and selectively adjustable spacer means for tilting said first plate means and the sample supporting means along at least one other axis for positioning and maintaining the sample-containing capillary on said first axis during rotation of said base means.

2. A fixture as claimed in claim 1, wherein pivot means are positioned between said first and second plate means at a location adjacent to said yieldable means for providing a point about which said sample supporting means on said first plate means is tiltable along at least said one other axis by said selectively adjustable spacer means, and wherein said yieldable means comprises spring means disposed between and attached to the first and second plate means at a location adjacent to a peripheral edge thereof for urging said first plate means toward said second plate means and for maintaining said first plate means in contact with said pivot means.

3. A fixture as claimed in claim 2, wherein said selectively adjustable spacer means comprises a pair of elongated threaded rod means threadedly coupled to and extending parallel to said boss means through said first plate means at locations on opposite sides of said boss means and bearing against the planar surface of said second plate means, wherein the rotation of one of said pair of elongated threaded rod means tilts said sample supporting means along a second axis perpendicular to said first axis, and wherein the rotation of the other of said pair of elongated rod means tilts said sample supporting means along a third axis perpendicular to both said first axis and said second axis.

4. A fixture as claimed in claim 1, wherein said sample supporting means is threadedly attached to said boss means, and wherein rotation of said sample supporting means on said boss means effects displacement the sample supporting means along said first axis and relative to said first and second plate means.

5. A fixture as claimed in claim 4, wherein bias means are arranged about said boss means to bear against said sample supporting means for maintaining said sample supporting means in the longitudinal position displaced to by the rotation of said sample supporting means.

6. A fixture as claimed in claim 3, wherein said pivot means comprises a ball disposed between said first and said second plate means at a location laterally spaced from and intermediate said elongated threaded rods.

7. A fixture as claimed in claim 6, wherein said spring means comprises a pair of tension springs positioned intermediate said ball and said elongated threaded rods for maintaining said first and second plate means in contact with said ball.

* * * * *